(12) United States Patent
Papac et al.

(10) Patent No.: US 8,485,972 B2
(45) Date of Patent: Jul. 16, 2013

(54) STRUCTURED ILLUMINATION PROBE AND METHOD

(75) Inventors: Michael J. Papac, Tustin, CA (US); Ronald T. Smith, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 358 days.

(21) Appl. No.: 12/913,868

(22) Filed: Oct. 28, 2010

(65) Prior Publication Data

US 2011/0112377 A1 May 12, 2011

Related U.S. Application Data

(60) Provisional application No. 61/260,143, filed on Nov. 11, 2009.

(51) Int. Cl.
*A61B 1/06* (2006.01)

(52) U.S. Cl.
USPC .......................................................... 600/249

(58) Field of Classification Search
USPC .......... 600/249, 478, 160–183; 606/4, 13–19; 385/16–25; 362/554, 572–575
See application file for complete search history.

(56) References Cited

U.S. PATENT DOCUMENTS

| | | |
|---|---|---|
| 4,423,931 A | 1/1984 | Shapiro |
| 4,699,140 A | 10/1987 | Holmes et al. |
| 4,730,910 A | 3/1988 | Humphrey |
| 4,738,521 A | 4/1988 | Volk |
| 4,900,144 A | 2/1990 | Kobayashi |
| 5,574,813 A | 11/1996 | Chudoba et al. |
| 7,048,379 B2 | 5/2006 | Miller et al. |
| 7,422,327 B2 | 9/2008 | Smith |
| 2001/0023346 A1 | 9/2001 | Loeb |
| 2005/0075628 A1* | 4/2005 | Cazzini et al. ................. 606/4 |
| 2005/0171408 A1* | 8/2005 | Parker ........................ 600/249 |
| 2006/0170867 A1 | 8/2006 | Koschmieder et al. |
| 2006/0184162 A1 | 8/2006 | Smith |
| 2007/0255264 A1 | 11/2007 | Hickingbotham |
| 2008/0080206 A1 | 4/2008 | Charles |
| 2009/0182313 A1 | 7/2009 | Auld |

* cited by examiner

*Primary Examiner* — Nicholas Woodall
*Assistant Examiner* — Melissa A Hall
(74) *Attorney, Agent, or Firm* — Keiko Ichiye

(57) ABSTRACT

A structured illumination probe is disclosed, one embodiment comprising: an optical fiber, to receive and transmit a light beam; a handpiece, coupled to the optical fiber; an optical element, comprising a distal optical fiber and a distal light guide, wherein the proximal ends of the distal optical fiber and the distal light guide can be selectably optically coupled to the optical fiber, for receiving the light beam and scattering the light beam to illuminate an area, and wherein the surface area of the proximal end of the distal light guide is greater than the surface area of the distal end of the optical fiber; an actuator, coupled to the handpiece, for selectably coupling the optical fiber to the distal optical fiber and the distal light guide; and a cannula, coupled to the handpiece, for housing and directing the optical fiber and the optical element.

19 Claims, 9 Drawing Sheets

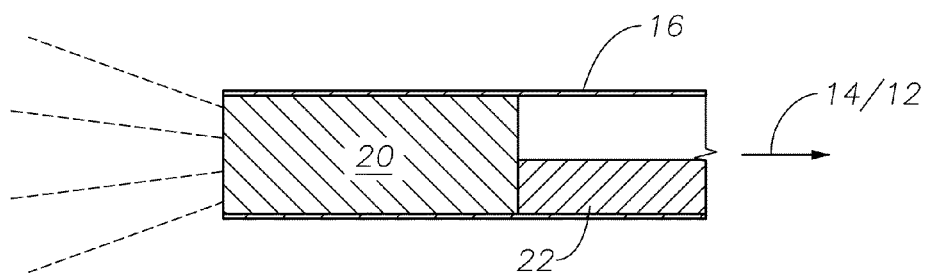
Fig. 5
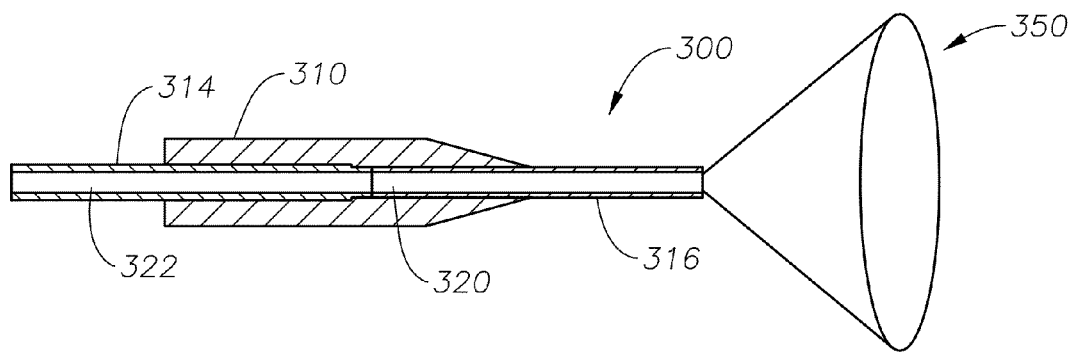
Fig. 6
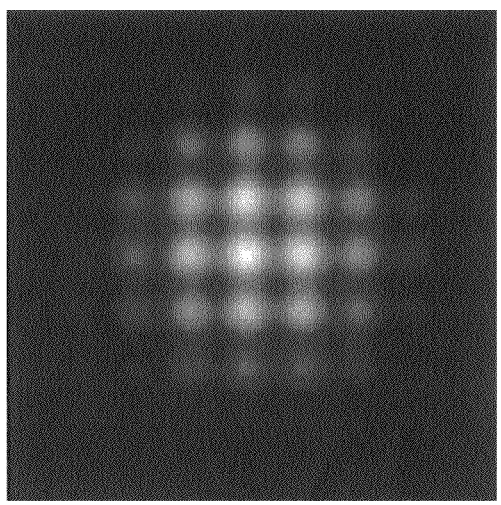 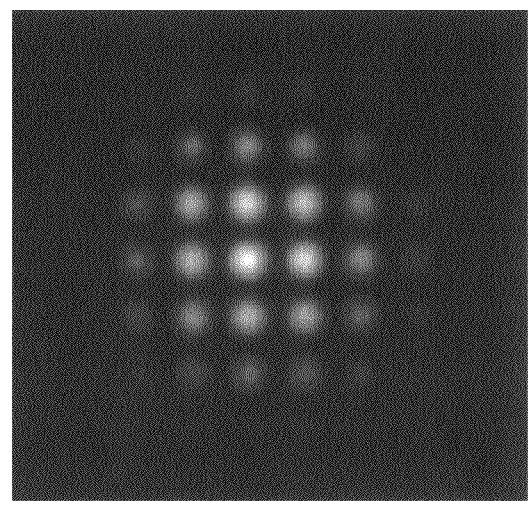
Fig. 7A                    Fig. 7B

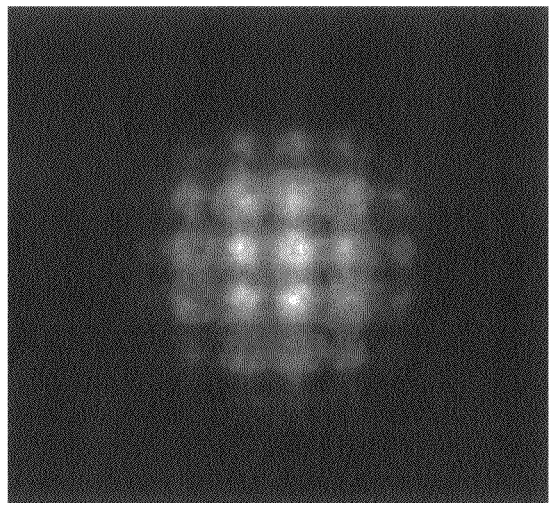
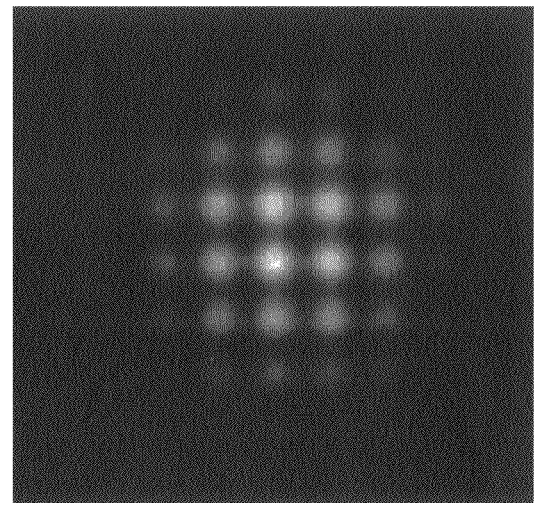
Fig. 8A          Fig. 8B
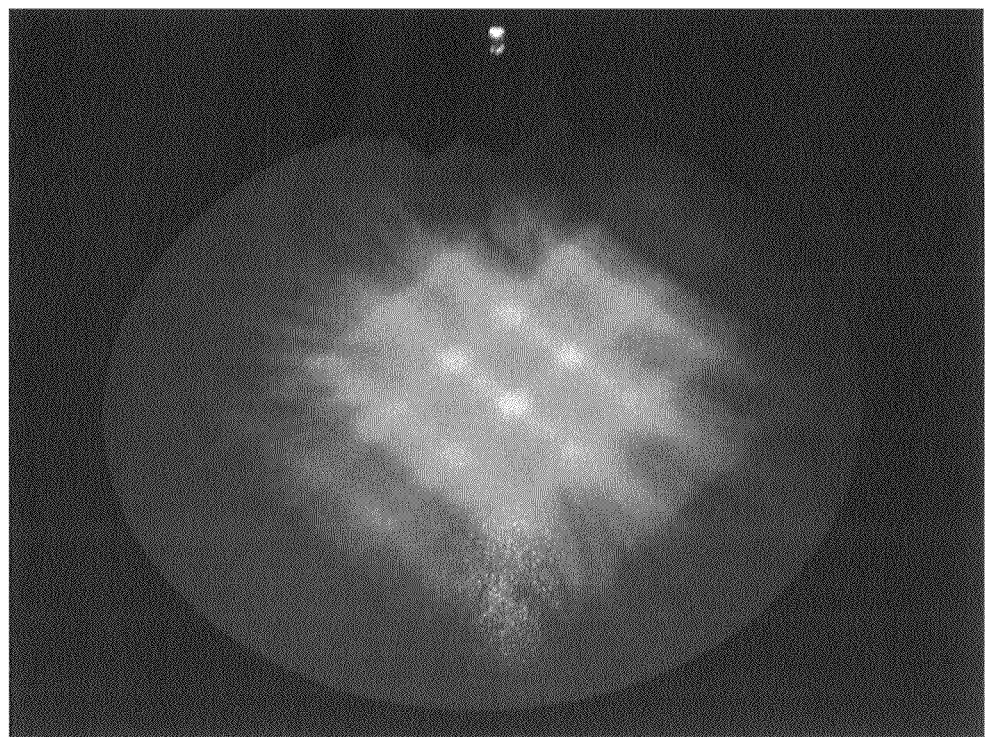
Fig. 9

Fig. 10
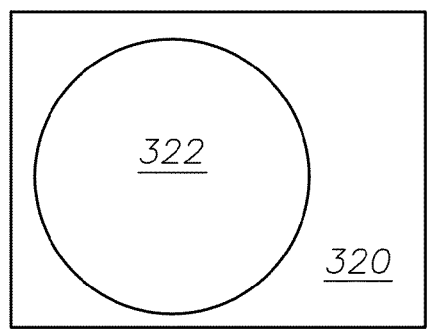
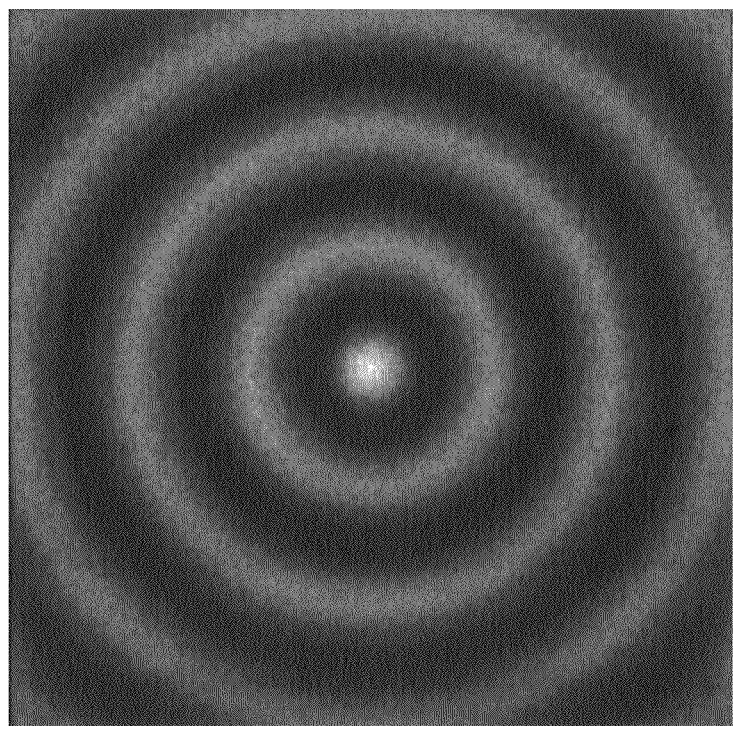
Fig. 11
Fig. 12
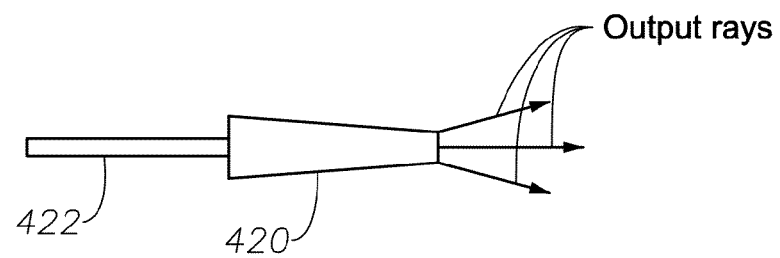

Patterned

STRUCTURED ILLUMINATION PROBE AND METHOD

TECHNICAL FIELD OF THE INVENTION

This application claims priority to U.S. Provisional Patent Application Ser. No. 61/260,143 filed on Nov. 11, 2009.

The present invention relates generally to surgical instrumentation and methods. In particular, the present invention relates to surgical systems and methods for illuminating an area during eye surgery. Even more particularly, the present invention relates to an illumination probe for providing structured illumination of a surgical field.

BACKGROUND OF THE INVENTION

In ophthalmic surgery, and in particular in vitreo-retinal surgery, surgeons rely on a variety of techniques to provide contrast in order to visualize features of interest on the retina. Techniques that are commonly used are brightfield imaging, darkfield imaging, and gradient field imaging. Gradient field imaging is created by illuminating a feature by partially overlapping an illumination spot so that parts of the feature are well lit by direct illumination and parts of the feature are dim or back-lit by scattered light, or through dynamic contrast by moving an illumination beam over the retinal feature. Because endoscopic illumination is provided by inserting a probe tip through a small incision, the fact that the probe may have to be articulated through the incision point, and that the illumination probe is at a finite angel of incidence relative to a viewing microscope, providing desirable contrast is difficult to realize in a practical surgical setting.

Patterned (structured) illumination can be used to provide contrast by which a surgeon can visualize ocular structures, such as retinal structures. To obtain desirable contrast illumination, it is preferable to create a regular pattern of illumination (irregular illumination patterns, such as spiral ring patterns or donut patterns, do not provide favorable contrast). However, illuminator probes that can efficiently provide structured illumination safe for use in ophthalmic procedures are unknown.

FIGS. 1 and 2 illustrate a prior art method of illuminating an off-axis portion of the fundus with a pattern of linear stripes. Because the stripe pattern illuminates the fundus at an off-axis incident angle, any bumps or depressions in the retinal surface show as curved stripes to an observer (FIG. 3). When viewed through a fundus camera and analyzed, the stripes can be used to derive information about the retinal topography. However, this type of prior art illumination device requires a bulky, off-axis illumination system attached to the fundus camera by a bracket and is not useful for microsurgery inside the eye.

Therefore, a need exists for an ophthalmic illuminator that can provide structured, safe illumination of a surgical field while overcoming the problems and disadvantages associated with prior art ophthalmic illuminators.

BRIEF SUMMARY OF THE INVENTION

The embodiments of the structured illumination probe and system and method for structured illumination of a surgical field of the present invention substantially meet these needs and others. One embodiment of the present invention is a surgical illumination system comprising: a light source for providing a light beam; an optical cable, comprising an optical fiber, optically coupled to the light source for receiving and transmitting the light beam; a handpiece, operably coupled to the optical cable; an optical element, comprising a distal optical fiber and a distal light guide, wherein a proximal end of each of the distal optical fiber and the distal light guide can be selectably optically coupled to a distal end of the optical fiber, for receiving the light beam and scattering the light beam to illuminate an area (e.g., a surgical site), and wherein the surface area of the proximal end of the distal light guide is greater than the surface area of the distal end of the optical fiber; an actuator, operably coupled to the handpiece, for selectably coupling the optical fiber to the distal optical fiber and the distal light guide; and a cannula, operably coupled to the handpiece, for housing and directing the optical fiber and the optical element.

The optical element can be a small-gauge light guide, which can be a square light guide, or a taper. For example, the optical element can be an acrylic taper or a 0.9 mm by 0.9 mm square light guide, and the optical fiber a 20 gauge optical fiber. The combination of an optical fiber with a distal end surface area smaller than the surface area of the optical element proximal end combines to spatially under-fill the entrance aperture of the optical element. The result is structured illumination output from the distal end of the optical element.

The cannula, optical element and the handpiece can be fabricated from biocompatible materials. The optical cable can comprise an optical connector for coupling the optical cable to the light source. These connectors can be standard illumination probe optical fiber connectors, as known to those having skill in the art, such as ACMI connectors. In some embodiments, a separate optical fiber in the handpiece can be coupled to the optical element proximal end and to the distal end of a fiber or fibers in the optical cable. The optical element, optical fiber and optical cable (i.e., the optical fiber(s) within the optical cable) should be of a compatible gauge so as to transmit the light beam from the light source to the surgical field. For example, all three elements could be of equal gauge.

Another embodiment of the present invention is a structured illumination probe, which can be a small-gauge illumination probe, comprising: an optical fiber, operable to receive a light beam and transmit the light beam to illuminate an area; a handpiece, operably coupled to the optical fiber; an optical element, a proximal end of the optical element optically coupled to a distal end of the optical fiber, for receiving the light beam and scattering the light beam to illuminate an area, wherein the surface area of the proximal end of the optical element is greater than the surface area of the distal end of the optical fiber; and a cannula, operably coupled to the handpiece, for housing and directing the optical fiber and the optical element The area can be a surgical site, such as the retina.

Other embodiments of the present invention can include a method for structured illumination of a surgical field using a structured illuminator in accordance with the teachings of this invention, and a surgical handpiece embodiment of the structured illuminator of the present invention for use in ophthalmic surgery. Another embodiment can comprise an illuminator for providing both structured and conventional illumination by selectively coupling either an optical element, as described above, or a distal optical fiber, to the optical fiber coupled to the light source. The distal optical fiber and the optical element can both be housed in the cannula and selected by means of, for example, a mechanical actuator. The distal optical fiber can be of the same diameter as the optical fiber. Further, embodiments of this invention can be incorporated within a surgical machine or system for use in ophthalmic or other surgery. Other uses for a structured illuminator designed in accordance with the teachings of this invention will be known to those having skill in the art.

BRIEF DESCRIPTION OF THE SEVERAL VIEWS OF THE DRAWINGS

A more complete understanding of the present invention and the advantages thereof may be acquired by referring to the following description, taken in conjunction with the accompanying drawings, in which like reference numbers indicate like features and wherein:

FIG. 5 is a diagrammatic representation of a close-up view of the distal end of an embodiment of a structured illuminator probe of this invention;

FIG. 6 is a diagrammatic representation of an embodiment of a structured illuminator in accordance with the teachings of this invention;

FIGS. 7A and 7B illustrate predicted structured illumination patterns that can be provided by embodiments of a structured illuminator probe in accordance with the teachings of this invention;

FIGS. 8A and 8B illustrate predicted structured illumination patterns that can be provided by other embodiments of a structured illuminator probe in accordance with the teachings of this invention;

FIG. 9 is an image of an actual rectilinear grid pattern of circular spots created by an embodiment of a structured illuminator in accordance with the teachings of the present invention;

FIG. 10 is a diagrammatic representation of a cross-sectional view of an embodiment of a structured illuminator probe of the present invention comprising a circular 20 gauge optical fiber under-filling a square light guide;

FIG. 11 shows a circular bulls-eye structured illumination pattern that can be provided by an embodiment of a structured illuminator probe in accordance with the teachings of this invention;

FIG. 12 is a diagrammatic representation of an embodiment of a structured illuminator in accordance with the teachings of this invention comprising a taper optical element;

DETAILED DESCRIPTION OF THE INVENTION

Figure 1:
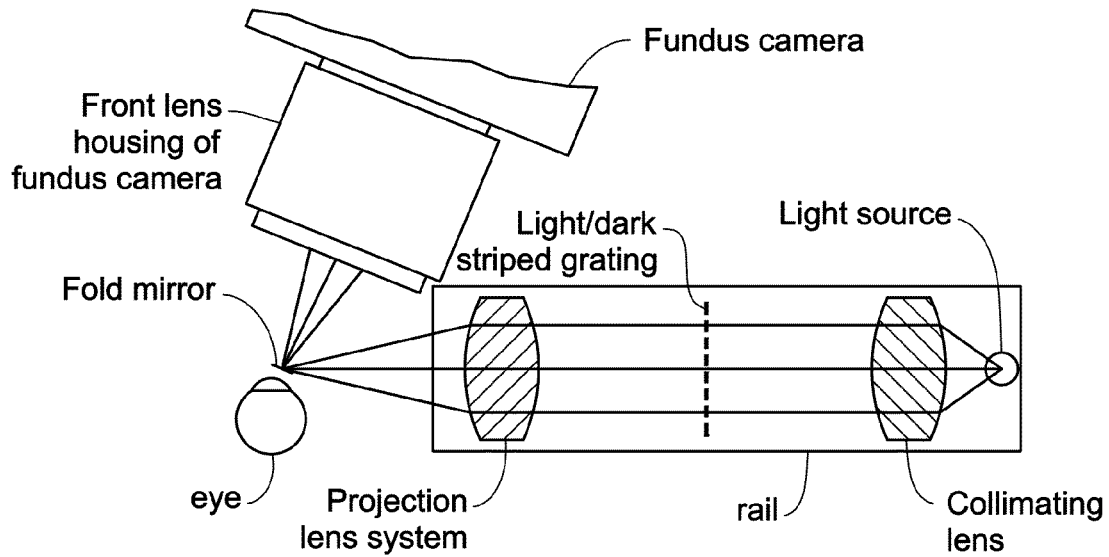
FIGS. 1-3 are diagrammatic representations of a prior art system and method for off-axis illumination of a fundus for retinal topography determination.
Figure 2:
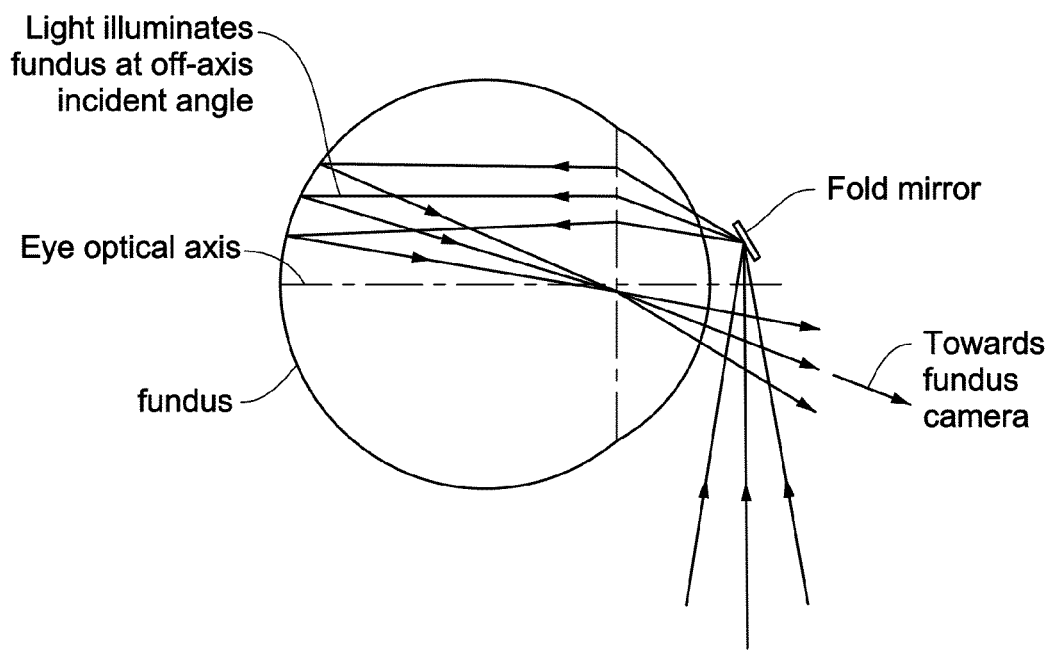
Figure 3:
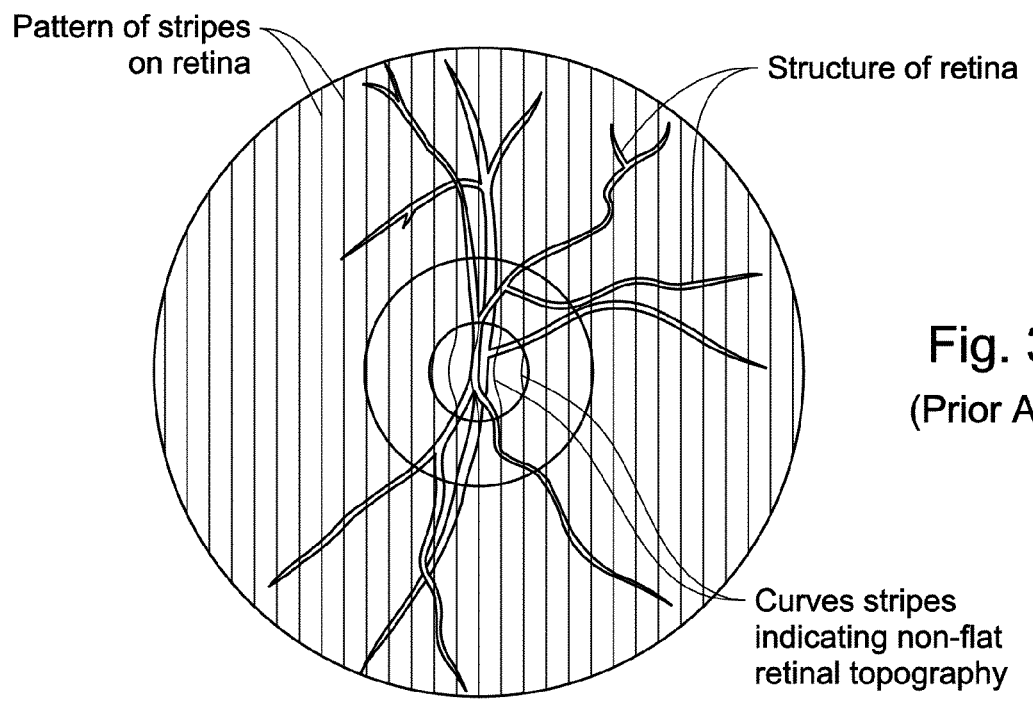

Preferred embodiments of the present invention are illustrated in the FIGURES, like numerals being used to refer to like and corresponding parts of the various drawings.

The various embodiments of the present invention provide for a small gauge (e.g., 19, 20, 25 or smaller gauge) optical fiber based endo-illuminator device for use in surgical procedures, such as in vitreo-retinal/posterior segment surgery. Embodiments of this invention can comprise a handpiece, such as the Alcon-Grieshaber Revolution-DSP™ handpiece sold by Alcon Laboratories, Inc., Fort Worth, Tex., connected to a small gauge cannula (e.g., 19, 20, 25 or smaller gauge). The inner dimension of the cannula can house an optical fiber, which can terminate in an optical coupling to an optical element, such as a light guide, or in a selectable light guide and distal optical fiber combination, in accordance with the teachings of this invention. Embodiments of the structured illuminator can be configured for use in the general field of ophthalmic surgery. However, it is contemplated and it will be realized by those skilled in the art that the scope of the present invention is not limited to ophthalmology, but may be applied generally to other areas of surgery where structured illumination may be desired.

Embodiments of the present invention provide for an illumination probe, system and method for producing structured illumination at a surgical site. The structured illumination can consist of, for example, a rectilinear grid patter on squares or circles, a series of parallel lines oriented at any desired angular orientation, a single or multiple ring pattern, or a combination of these patterns. The patterned (structured) illuminator output is created with minimal loss to the overall probe transmission by optically coupling a light guide to the distal end of a delivery optical fiber so that the entrance aperture (proximal end surface) of the light guide is spatially under-filled. The degree of under-fill, the asymmetry of the under-fill, the shape of the light guide and manicuring the distal end of the delivery fiber into different shapes (e.g., circle, ellipse, or near-square) can provide for design control of the illuminator output pattern. Embodiments of the structured illuminator of this invention can be directional or chandelier-type illuminators, or other ophthalmic illuminator types as are known to those having skill in the art. Embodiments of the structured illuminator of this invention can provide for improved visualization of retinal structures and/or retinal surface topology.

Embodiments of the illuminator of the present invention can produce structured illumination in the form of a regular or irregular grid patter of shapes (e.g., circles, squares, ellipses, rectangles or more complex shapes) from the distal end of the illuminator cannula. Other embodiments can produce structured illumination in the form of a linear pattern, a symmetric or asymmetric ring (e.g., a bulls-eye) pattern, and, in at least one embodiment, both structured and conventional illumination, or multiple structured illumination patterns, simultaneously or sequentially.

An embodiment of the structured illuminator of this invention can comprise an optical fiber, an optical element, a stem (cannula) and a handpiece fabricated from biocompatible polymeric materials, such that the invasive portion of the structured illuminator can be made as a low-cost disposable surgical item. Unlike the prior art, the embodiments of the structured illuminator of this invention can provide enhanced contrast of retinal structures during vitreo-retinal surgery using only structured illumination, or in a dual-function embodiment, a combination of structured and conventional illumination, either simultaneously or sequentially. Embodiments of this invention fabricated from biocompatible polymeric materials can be integrated into a low cost, articulated handpiece mechanism, such that these embodiments can comprise an inexpensive disposable illuminator instrument.

Figure 4:
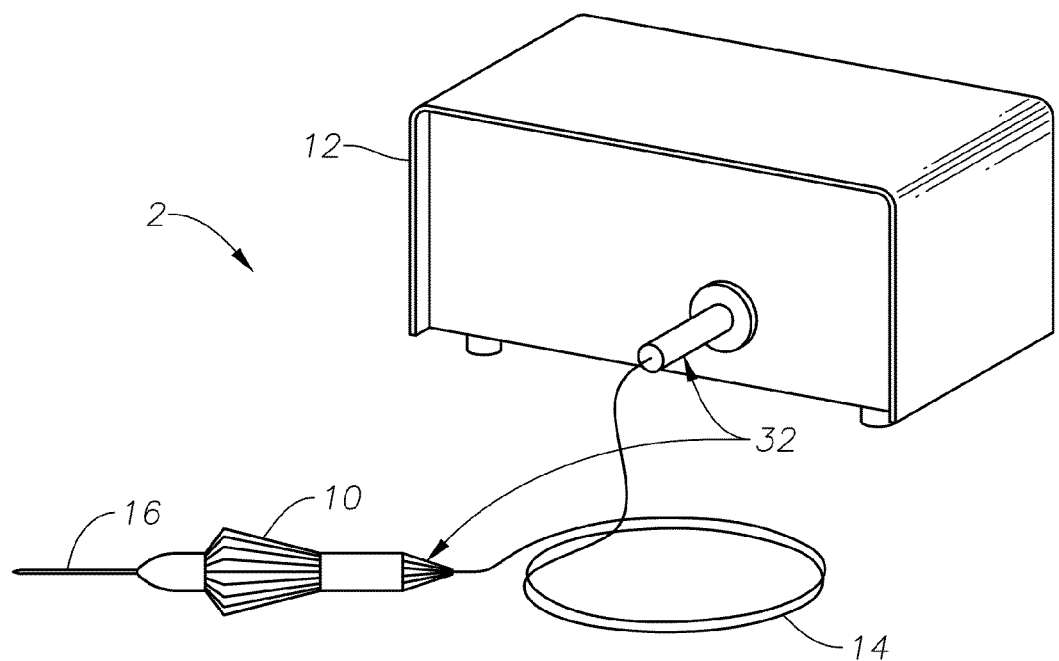
FIG. 4 is a diagrammatic representation of an embodiment of a system for structured illumination in accordance with the teachings of this invention.

FIG. 4 is a diagrammatic representation of a surgical system 2 comprising a handpiece 10 for delivering a beam of light from a light source 12 through cable 14 to a stem 16.

Cable 14 can be any gauge fiber optic cable as known in the art, such as a cable having 19, 20, or 25 gauge fiber. Further, cable 14 can comprise a single optical fiber or a plurality of optical fibers optically coupled to light source 12 to receive and transmit the light beam to an optical fiber 22 within stem 16 through handpiece 10. Stem 16 is configured to house an optical fiber 22 and an optical element 20 at the distal end of stem 16, as is more clearly illustrated in FIGS. 5-6. Coupling system 32 can comprise an optical fiber connector at each end of cable 14 to optically couple light source 12 to optical fiber 22 within handpiece 10, as discussed more fully below.

FIG. 5 is a more detailed diagram illustrating one embodiment of optical element 20. FIG. 5 provides a magnified view of the distal end of stem 16. Stem 16 is shown housing fiber 22 and optical element 20. Optical element 20 is optically coupled to fiber 22, which can itself be optically coupled to fiber optic cable 14. In some embodiments, fiber optic cable 14 can comprise an optical fiber that extends from the light source coupling through the handpiece 10 and is optically coupled directly to optical element 20. For these embodiments, a separate fiber 22 is not used. The distal end surface of optical fiber 22/14 can be optically bonded to the proximal end surface of optical element 20, as described more fully below. Optical element 20 can comprise an optical grade machined or injection-molded plastic or other polymer light guide or taper, for example.

When implemented within handpiece 10, fiber 22 is of a gauge compatible with the gauge of fiber optic cable 14, such that it can receive and transmit light from fiber optic cable 14. Handpiece 10 can be any surgical handpiece as known in the art, such as the Revolution-DSP™ handpiece sold by Alcon Laboratories, Inc. of Fort Worth, Tex. Light source 12 can be a xenon light source, a halogen light source, an LED light source, or any other light source capable of providing light for delivery through an optical fiber. Stem 16 can be a small gauge cannula, such as within the range of 18 to 30 gauge, as known to those having skill in the art. Stem 16 can be stainless steel or a suitable biocompatible polymer (e.g., PEEK, polyimide, etc.) as known to those having skill in the art.

Light source 12 can be optically coupled to handpiece 10 (i.e., to fiber 22) using, for example, standard ACMI optical fiber connectors at the ends of fiber optic cable 14. This allows for the efficient coupling of light from the light source 12 through fiber optic cable 14 to the handpiece 10 and finally emanating from optical element 20 at the distal end of the stem 16. Light source 12 may comprise filters, as known to those skilled in the art, to reduce the damaging thermal effects of absorbed infrared radiation originating at the light source. The light source 12 filter(s) can be used to selectively illuminate a surgical field with different colors of light, such as to excite a surgical dye.

Spatial patterning in light emitted from multi-mode fibers with at least some degree of radial symmetry can occur whenever the following occurs: the luminance of the light at the entrance aperture to the fiber is asymmetrically spatially non-uniform; if the fiber is not straight throughout its length (i.e., at least a portion is tapered) then the spatial non-uniformity of the luminance at the entrance aperture to the fiber need not be asymmetric; or if some feature or obstruction prevents all rays of light from passing through the fiber with 100% efficiency (such as an absorptive patch in a region of cladding on the side of the light pipe). These phenomenons can occur in prior art illumination probes, but are usually considered objectionable for general illumination. However, it has been found that certain structured illumination, such as that provided by the embodiments of the present invention, can be advantageous for enhancing the ability of an observer (e.g., a surgeon) to discern retinal features, such as those retinal features with raised or depressed areas relative to the surrounding retinal tissue.

FIG. 6 shows one embodiment of a structured illuminator probe in accordance with the present invention. Structured illuminator probe 300 comprises handpiece 310, and optical cable 314, comprising a protective outer covering and an optical fiber 322, operably coupled to handpiece 310. Optical fiber 322 can be optically coupled to a light source, not shown, for receiving a light beam and transmitting the light beam to optical element 320. Optical element 320 and the distal end of optical fiber 322 are housed within cannula 316. Optical element 320 receives the light beam from optical fiber 322 and provides as an output at its distal end patterned illumination 350. As can be seen in FIG. 6, optical fiber 320 has a smaller cross-sectional area than optical element 320 (i.e., the surface area of the distal end surface of optical fiber 322 is less than the surface area of the proximal end surface of optical element 320). Optical element 320 can have a circular, square, elliptical or other cross-section shape and can be a light guide or taper.

The cannula (stem) 316 can be made of steel and can be smoothly curved so as to contact the optical element 320 only at the extreme distal end, as shown in FIG. 5, or can contact the optical element at any point along its length. At the point (s) of contact, the optical element 320 can be bonded to the stem 316 by means of adhesive to provide mechanical strength and a seal to prevent liquid from the eye from entering into any air gap between the optical element 320 and the stem 316. Optical element 320 can also be coupled to stem 316 such that its distal end extends out slightly beyond the distal end of stem 316. Optical fiber 322 and optical element 320 can be optically coupled by simple contact, using optical adhesive or by other bonding techniques as are known to those having skill in the art, such that optical fiber 322 is asymmetrically coupled to the optical element 320 to create structured output pattern 350.

FIGS. 7A and 7B illustrate predicted structured illumination patterns comprising a rectilinear grid of squares that can be provided by an embodiment of the illuminator probe of the present invention. The patterns created in FIGS. 7A and 7B are created by an embodiment having a distal end of optical fiber 322 manicured into a square and coupled to an optical element 320 comprising a larger square light guide. FIG. 7A represents a high-density array of square images and FIG. 7B represents a low density array of square images.

FIGS. 8A and 8B illustrate predicted structured illumination patterns comprising a rectilinear grid of squares that can be provided by another embodiment of the illuminator probe of the present invention. The patterns shown in FIGS. 8A and 8B are created by an embodiment having an unmanicured optical fiber 322 having a conventional circular end coupled to an optical element 320 comprising a larger surface area square light guide. FIG. 8A represents a high-density array of square images and FIG. 8B represents a low density array of square images.

FIG. 9 is an image of an actual rectilinear grid pattern of circular spots created by an embodiment of the structured illuminator of the present invention comprising a circular 20 gauge optical fiber 322 under-filling a 0.9 mm by 0.9 mm square light guide 320 as shown in cross-sectional detail in FIG. 10. Light streaks at the perimeter of the output pattern (light beam) can be removed by aperturing the output of the light guide 320.

Embodiments of the structured illuminator of the present invention can also provide circular bulls-eye illumination patterns, such as shown in FIG. 11. Such a pattern can be created by an optical element 420 comprising a taper optically coupled to the optical fiber 422, as shown in FIG. 12. Optical fiber 422 and optical element 420 of FIG. 12 are analogous to and provide functions as described for elements 20, 22 and 320, 322 in previous FIGUREs. As shown in FIG. 12, optical fiber 422 transmits a light beam (as previously described in regards to other embodiments) to optical element 420, underfilling the entrance aperture of optical element (taper) 420. Optical element 420 can be an acrylic taper.

Figure 13A:
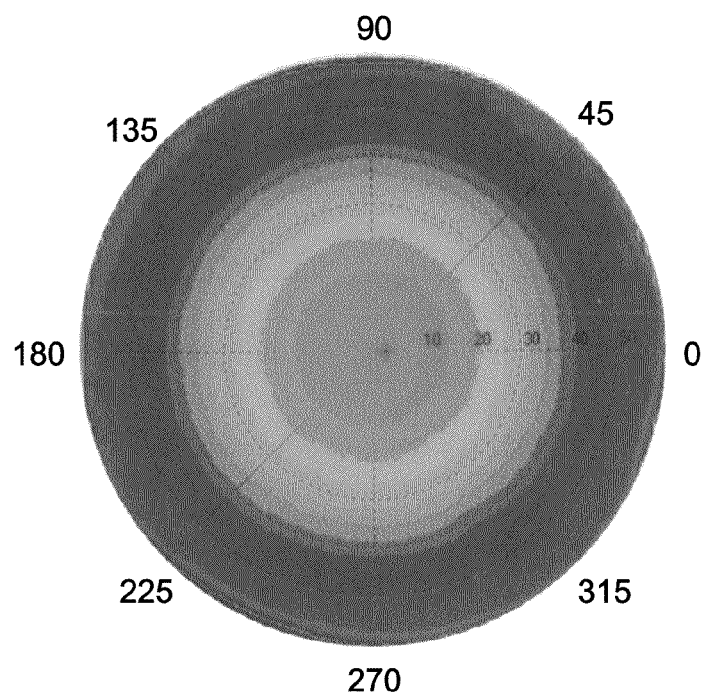
FIGS. 13A-13C illustrate the patterned and unpatterned output of an embodiment of a structured illuminator probe having an optical element coupled to a high NA source in accordance with the teachings of this invention.
Figure 13B:
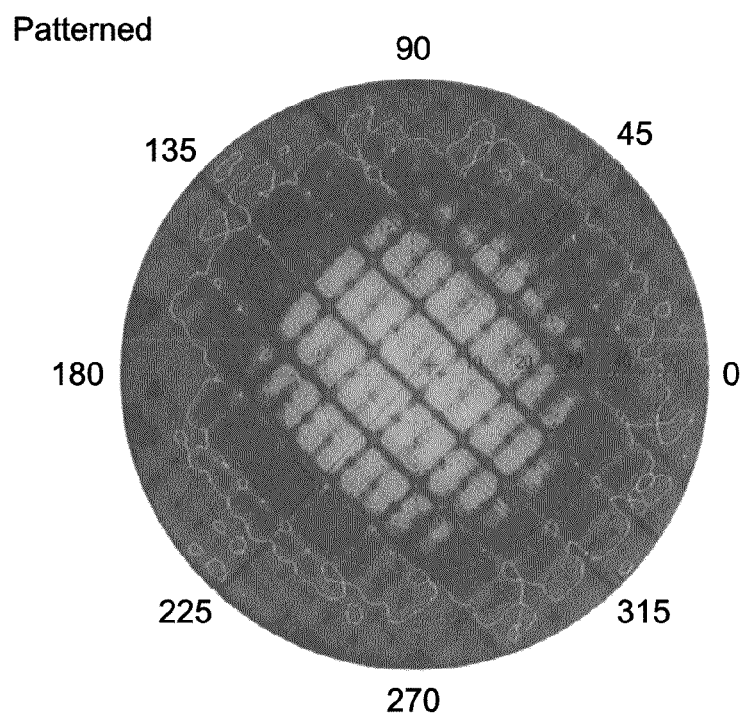
Figure 13C:
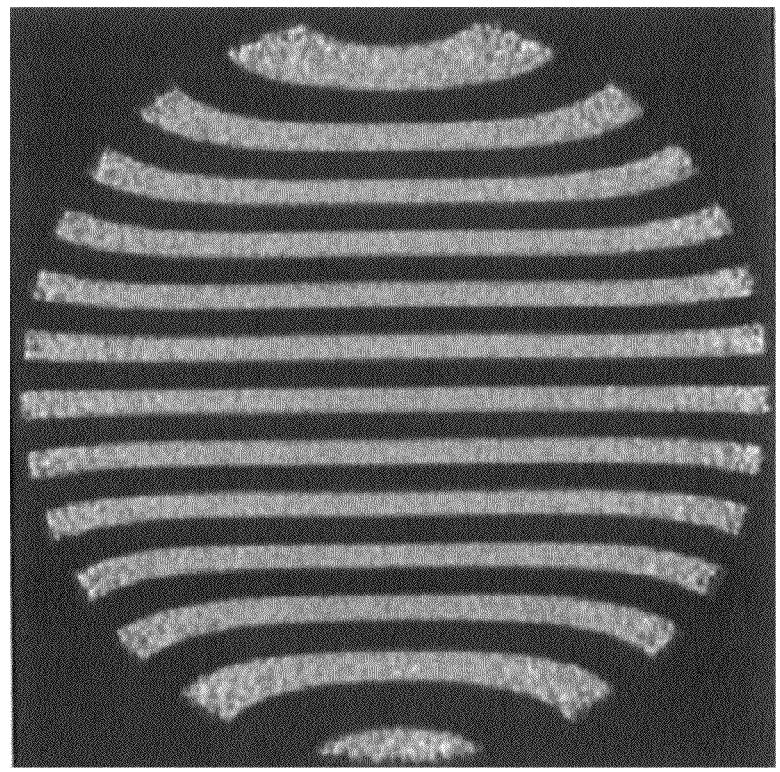
Figure 14:
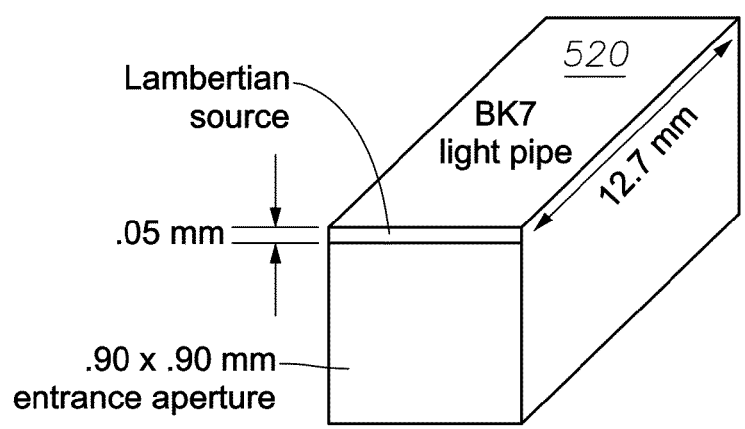
FIG. 14 is a diagrammatic representation of an embodiment of a structured illuminator probe of the present invention comprising a square light is pipe optical element.

The embodiments discussed above provide structured illumination using standard optical fibers typically having an NA (numerical aperture) limited to 0.5 or 0.63. Other embodiments can instead comprise an optical element optically coupled to a high NA source, such as an LED or high NA photonic crystal or photonic bandgap optical fiber. In such embodiments, the pattern will extend throughout the entire NA of the source coupled to the optical element. FIGS. 13A-13C illustrate the patterned and unpatterned output of such an embodiment. FIG. 13A shows the bare output from an LED source without a distal light guide in place. FIGS. 13B and 13C show the patterned output created by the same LED source with a light guide in place, in this example underfilling a square cross-sectioned lightpipe (optical element) using a Lambertian emitting LED source. FIG. 14 is a diagrammatical representation of such an embodiment, showing an optical element 520 comprising a square light pipe. The light pipe 520 is shown being underfilled by a Lambertian LED light source.

Figure 15A:
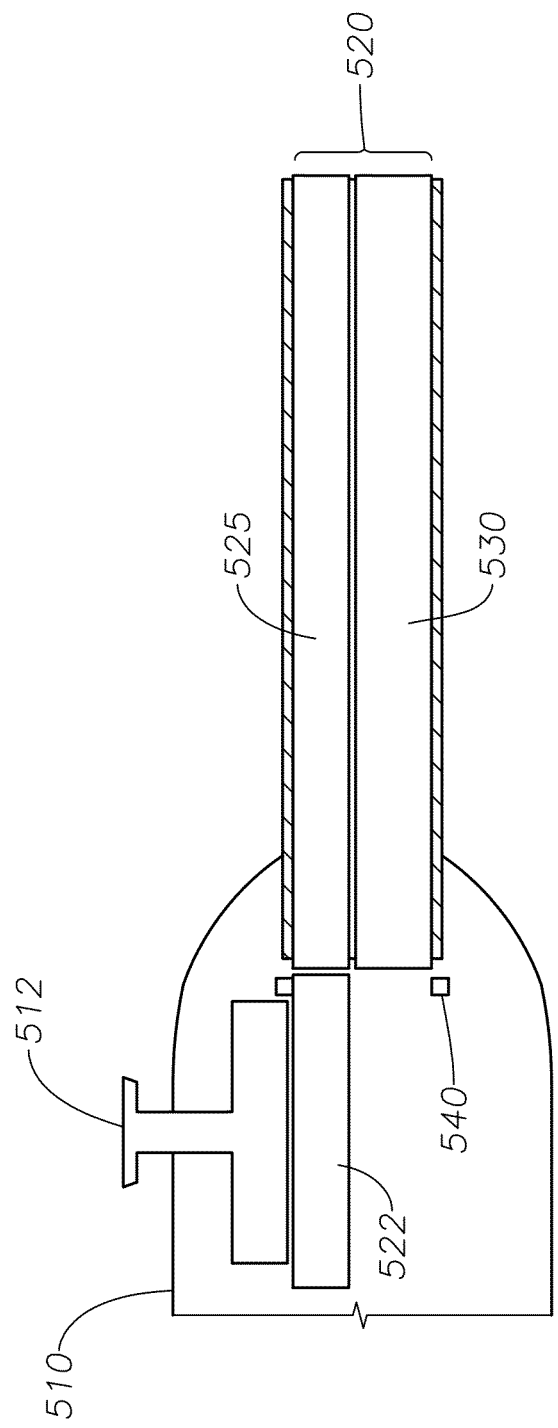
FIGS. 15A and 15B are diagrammatic representations of a dual-function embodiment of a structured illuminator in accordance with the teachings of the present invention.
Figure 15B:
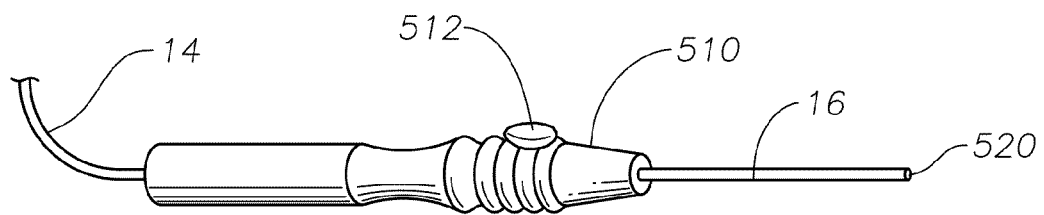

FIGS. 15A and 15B are diagrammatical representations of a dual-function embodiment of the structured illuminator of the present invention. In this embodiment, handpiece 510 includes an actuator 512, which can be a mechanical, electrical, magnetic or other actuation mechanism as known to those having skill in the art, for selecting between two distal output paths of optical element 520. In this embodiment, optical element 520 comprises a distal optical fiber 525 to provide for standard illumination and a distal light guide 530 to provide structured illumination in accordance with the teachings described herein. In operation, a user can select between the two output paths by means of actuator 512 which can, as, for example, is shown in FIG. 15A, mechanically align delivery optical fiber 522 with either distal optical fiber 525 or distal light guide 530. Precision stops 540 ensure proper alignment between delivery optical fiber 522 and either distal optical fiber 525 or distal light guide 530. A user of such an embodiment of the present invention thus can have at his disposal a dual-function probe which can provide either type of illumination on demand without requiring an instrument change.

Figure 16:
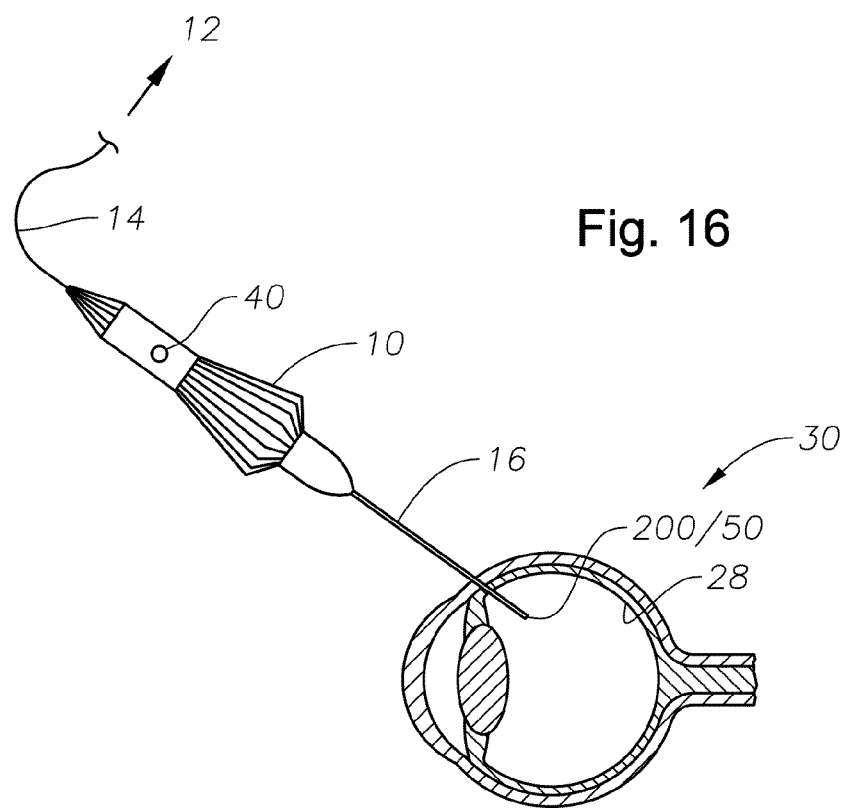
FIG. 16 is a diagram illustrating the use of an embodiment of a wide-angle illuminator of the present invention in ophthalmic surgery.

FIG. 16 illustrates the use of one embodiment of the structured illuminator of this invention in an ophthalmic surgery. In operation, handpiece 10 delivers a beam of light through stem 16 (via optical fiber 22/14) and through optical element 20 to illuminate a retina 28 of an eye 30. The light delivered through handpiece 10 to the optical element 20 is generated by light source 12 and delivered to illuminate the retina 28 by means of fiber optic cable 14 and coupling system 32. Optical element 20 is operable to provide structured illumination in a desired pattern on the retina to provide the contrast needed for useful visualization of retinal features.

Although the present invention has been described in detail herein with reference to the illustrated embodiments, it should be understood that the description is by way of example only and is not to be construed in a limiting sense. It is to be further understood, therefore, that numerous changes in the details of the embodiments of this invention and additional embodiments of this invention will be apparent to, and may be made by, persons of ordinary skill in the art having reference to this description. It is contemplated that all such changes and additional embodiments are within the spirit and true scope of this invention as claimed below. Thus, while the present invention has been described in particular reference to the general area of ophthalmic surgery, the teachings contained herein apply equally wherever it is desirous to provide structured illumination of a surgical site.

What is claimed is:

1. A structured illumination probe, comprising:
    an optical fiber, operable to receive and transmit a light beam; a handpiece, operably coupled to the optical fiber;
    an optical element, comprising a distal optical fiber and a distal light guide, the distal optical fiber corresponding to a first output path of the optical element and the distal light guide corresponding to a second output path of the optical element distinct from the first output path, wherein a proximal end of each of the distal optical fiber and the distal light guide can be selectably optically coupled to a distal end of the optical fiber, for receiving the light beam and scattering the light beam to illuminate an area, and wherein the surface area of the proximal end of the distal light guide is greater than the surface area of the distal end of the optical fiber;
    an actuator, operably coupled to the handpiece, for selectably coupling the optical fiber to the distal optical fiber and the distal light guide to select between the first output path and the second optical path; and
    a cannula, operably coupled to the handpiece, for housing and directing the optical fiber and the optical element.

2. The structured illumination probe of claim 1, wherein the distal light guide is machined or injection-molded plastic.

3. The structured illumination probe of claim 1, wherein the distal light guide is a 19, 20 or 25 gauge light guide.

4. The structured illumination probe of claim 1, wherein the cannula and the handpiece are fabricated from biocompatible materials.

5. The structured illumination probe of claim 1, wherein the optical fiber is optically coupled at a proximal end to an optical cable, wherein the optical cable is operably coupled to the light source to transmit the light beam to the optical fiber.

6. The structured illumination probe of claim 5, wherein the optical cable gauge and the optical fiber gauge are equal.

7. The structured illumination probe of claim 1, wherein the light source is a xenon light source.

8. The structured illumination probe of claim 1, wherein the light source is a LED light source.

9. The structured illumination probe of claim 1, further comprising a set of precision stops to ensure alignment between the optical fiber and the distal optical fiber and the distal light guide.

10. The structured illumination probe of claim 1, wherein the distal light guide comprises a taper.

11. A structured illumination system comprising:
    a light source for providing a light beam;
    an optical cable, comprising an optical fiber, optically coupled to the light source for receiving and transmitting the light beam;
    a handpiece, operably coupled to the optical cable;
    an optical element, comprising a distal optical fiber and a distal light guide, the distal optical fiber corresponding to a first output path of the optical element and the distal light guide corresponding to a second output path of the optical element distinct from the first output path, wherein a proximal end of each of the distal optical fiber and the distal light guide can be selectably optically coupled to a distal end of the optical fiber, for receiving the light beam and scattering the light beam to illuminate an area, and wherein the surface area of the proximal end of the distal light guide is greater than the surface area of the distal end of the optical fiber;

an actuator, operably coupled to the handpiece, for selectably coupling the optical fiber to the distal optical fiber and the distal light guide to select between the first output path and the second optical path;

and a cannula, operably coupled to the handpiece, for housing and directing the optical fiber and the optical element.

12. The structured illumination system of claim 11, wherein the distal light guide is machined or injection-molded plastic.

13. The structured illumination system of claim 11, wherein the distal light guide is a 19, 20 or 25 gauge light guide.

14. The structured illumination system of claim 11, wherein the cannula and the handpiece are fabricated from biocompatible materials.

15. The structured illumination system of claim 11, further comprising a seal at the distal end of the cannula between the optical element and the cannula.

16. The structured illumination system of claim 11, wherein the light source is a xenon light source.

17. The structured illumination system of claim 11, wherein the light source is a LED light source.

18. The structured illumination system of claim 11, further comprising a set of precision stops to ensure alignment between the optical fiber and the distal optical fiber and the distal light guide.

19. The structured illumination system of claim 11, wherein the distal light guide comprises a taper.

* * * * *